United States Patent
Mahon et al.

(10) Patent No.: US 9,931,523 B2
(45) Date of Patent: Apr. 3, 2018

(54) RF POWER CONTROLLER FOR ULTRASOUND THERAPY SYSTEM

(75) Inventors: Cameron Mahon, Georgetown (CA); Nicolas Yak, Ontario (CA); Rajiv Chopra, Toronto (CA); Mathew Asselin, Toronto (CA); Michael Bronskill, Toronto (CA)

(73) Assignee: Profound Medical, Inc., Mississauga, ON (CA)

( * ) Notice: Subject to any disclaimer, the term of this patent is extended or adjusted under 35 U.S.C. 154(b) by 1524 days.

(21) Appl. No.: 12/932,923

(22) Filed: Mar. 9, 2011

(65) Prior Publication Data

US 2011/0270366 A1    Nov. 3, 2011

Related U.S. Application Data

(60) Provisional application No. 61/311,847, filed on Mar. 9, 2010.

(51) Int. Cl.
| | |
|---|---|
| *A61H 1/00* | (2006.01) |
| *A61H 1/02* | (2006.01) |
| *A61H 5/00* | (2006.01) |
| *A61N 7/00* | (2006.01) |
| *A61B 17/225* | (2006.01) |
| *A61N 7/02* | (2006.01) |

(52) U.S. Cl.
CPC .............. *A61N 7/00* (2013.01); *A61B 17/225* (2013.01); *A61N 7/022* (2013.01); *A61N 2007/0095* (2013.01)

(58) Field of Classification Search
None
See application file for complete search history.

(56) References Cited

U.S. PATENT DOCUMENTS

| 5,295,484 A | 3/1994 | Marcus et al. |
| 5,593,415 A | 1/1997 | Adrian |

(Continued)

OTHER PUBLICATIONS

Chopra et al., Med. Phys., 27(6): 1281-1286, 2000.

(Continued)

*Primary Examiner* — Amanda Lauritzen Moher
*Assistant Examiner* — Shahdeep Mohammed
(74) *Attorney, Agent, or Firm* — Intrinsic Law Corp.

(57) ABSTRACT

An apparatus for driving and controlling ultrasonic elements includes a computer-based host unit that determines driving characteristics with which to drive the ultrasonic elements; a microprocessor-based controller that receives an output from the host and provides signals representing a frequency and/or an amplitude characteristic; a frequency control circuit receiving the frequency characteristic signal; an amplitude control circuit receiving the amplitude characteristic signal; an RF amplifier acting on an output from the frequency and/or the amplitude control circuits to provide an amplified output signal corresponding to the frequency and/or amplitude characteristic; a coupling circuit that couples the amplified output signal to the ultrasonic elements and provides a forward output signal to a first RF detector circuit and a reverse output signal to a second RF detector circuit; and an analog-to-digital converter that receives an output of the RF detector circuits and provides a corresponding converted output to the controller.

14 Claims, 4 Drawing Sheets

(56) References Cited

U.S. PATENT DOCUMENTS

| | | |
|---|---|---|
| 5,601,526 A | 2/1997 | Chapelon et al. |
| 5,620,479 A | 4/1997 | Diederich |
| 5,647,361 A | 7/1997 | Damadian |
| 5,733,315 A | 3/1998 | Burdette et al. |
| 6,050,943 A | 4/2000 | Stayton et al. |
| 6,007,257 A | 6/2000 | Edwards et al. |
| 6,122,551 A | 9/2000 | Rudie et al. |
| 6,217,530 B1 * | 4/2001 | Martin ............. A61B 17/22004 600/439 |
| 6,379,320 B1 | 4/2002 | Lafon et al. |
| 6,393,314 B1 | 5/2002 | Watkins et al. |
| 6,418,337 B1 | 7/2002 | Torchia et al. |
| 6,432,067 B1 | 8/2002 | Martin et al. |
| 6,490,488 B1 | 12/2002 | Rudie et al. |
| 6,500,121 B1 | 12/2002 | Stayton et al. |
| 6,516,211 B1 | 2/2003 | Acker et al. |
| 6,522,142 B1 | 2/2003 | Freundlich |
| 6,537,306 B1 | 3/2003 | Burdette et al. |
| 6,542,767 B1 | 4/2003 | McNichols et al. |
| 6,559,644 B2 | 5/2003 | Freundlich et al. |
| 6,582,381 B1 | 6/2003 | Yehezkeli et al. |
| 6,589,174 B1 | 7/2003 | Chopra et al. |
| 6,618,608 B1 | 9/2003 | Watkins et al. |
| 6,618,620 B1 | 9/2003 | Freundlich et al. |
| 6,623,430 B1 | 9/2003 | Stayton et al. |
| 6,671,535 B1 | 12/2003 | McNichols et al. |
| 6,692,450 B1 | 2/2004 | Coleman |
| 6,692,518 B2 | 2/2004 | Carson |
| 6,735,461 B2 | 5/2004 | Vitek et al. |
| 6,746,465 B2 | 6/2004 | Diederich et al. |
| 6,755,849 B1 | 6/2004 | Gowda et al. |
| 6,818,012 B2 | 11/2004 | Ellingboe |
| 7,135,029 B2 | 11/2006 | Makin et al. |
| 7,167,741 B2 | 1/2007 | Torchia et al. |
| 7,229,411 B2 | 6/2007 | Stayton et al. |
| 7,344,529 B2 | 3/2008 | Torchia et al. |
| 7,473,224 B2 | 1/2009 | Makin |
| 7,771,418 B2 | 8/2010 | Chopra et al. |
| 7,806,892 B2 | 10/2010 | Makin et al. |
| 7,951,182 B2 | 5/2011 | Stelea et al. |
| 7,993,289 B2 | 8/2011 | Quistgaard et al. |
| 8,021,406 B2 | 9/2011 | Cazzini et al. |
| 8,025,688 B2 | 9/2011 | Diederich et al. |
| 2003/0018266 A1 | 1/2003 | Makin et al. |
| 2003/0069502 A1 | 4/2003 | Makin et al. |
| 2003/0092988 A1 | 5/2003 | Makin |
| 2004/0172083 A1 * | 9/2004 | Penner .................... 607/35 |
| 2004/0206365 A1 * | 10/2004 | Knowlton ............. A61B 18/14 128/898 |
| 2006/0052697 A1 * | 3/2006 | Hossack et al. .......... 600/437 |
| 2006/0241442 A1 | 10/2006 | Barthe et al. |
| 2007/0239062 A1 | 10/2007 | Chopra et al. |
| 2007/0249938 A1 * | 10/2007 | Shields ................... 600/447 |
| 2008/0242970 A1 | 10/2008 | Minagawa et al. |
| 2009/0143775 A1 | 6/2009 | Rizoiu et al. |
| 2009/0171185 A1 | 7/2009 | Chou et al. |
| 2009/0264798 A1 * | 10/2009 | Hynynen et al. ............. 601/2 |
| 2010/0204694 A1 * | 8/2010 | Mehta et al. ............... 606/42 |
| 2011/0112405 A1 * | 5/2011 | Barthe et al. ............ 600/459 |

OTHER PUBLICATIONS

Chopra et al., IEEE Transactions on Ultrasonics, Ferroelectrics, and Frequency Control, 50(7):881-889, 2003.
Diederich et al., Med. Phys., 31(2):405-413, 2004.
Kowalski et al., Phys. Med. Biol., 48:633-651, 2003.
Lafon et al., Ultrasonics, 36:683-687, 1998.
Lafon et al., Ultrasound Med. Biol., 30(1):113-122, 2004.
McNichols et al., Lasers Surg. Med., 34:48-55, 2004.
Ross et al., Phys. Med. Biol., 49:189-204, 2004.
Smith et al., Int. J. Hyperthermia, 17(3): 271-282, 2001.
Vanne et al., Phys. Med. Biol., 48: 31-43, 2003.

* cited by examiner

40

1. Iterate through all 12 channels and...
    1. Calculate Pnet = Vfwd-Vrev
    2. Compare Pnet to desired Pnet value stored in memory (received from host)
    3. if PnetActual – PnetDesired is > tolerance, increment or decrement the byte command depending on whether we're over or under
    4. Update the proper digipot and digipot history short immediately.

Fig. 4

RF POWER CONTROLLER FOR ULTRASOUND THERAPY SYSTEM

RELATED APPLICATIONS

The present application is related to and claims priority under 35 USC § 120 to U.S. Provisional Application No. 61/311,847, bearing the present title, filed on Mar. 9, 2010, which is hereby incorporated by reference.

TECHNICAL FIELD

The present application relates to ultrasound therapy systems, and particularly to the control of and provisioning of electrical power to ultrasonic treatment apparatus of such systems.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes. With proper monitoring of the heating effect, ultrasound therapy systems can be used to treat harmful cells and to controllably destroy cancerous tumors.

As known to those skilled in the art, ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezo-electric transducer crystal material (lead zirconate titanate, PZT) which comes in several forms.

In general, a higher power electrical supply input results in a greater acoustic (ultrasonic) output from the transducers. However, the precise form of the optimal electrical supply power to ultrasound transducer elements and systems can be difficult to determine in advance of use of the systems. Also, it is difficult to determine the exact power and efficiency of ultrasound therapy systems using present techniques. In addition, it has been difficult or impossible to accurately measure the electrical input power and effectiveness of electrically-driven ultrasound therapy transducers and systems. Factors such as design and material variability, as well as real-time variability within the system and the patient can cause drift or uncertainty in the electrical behavior of ultrasound treatment systems.

It is therefore useful to have improved ways of provisioning electrical power to ultrasound therapy systems and transducers. It is also useful to be able to measure the electrical power needs and usages of such transducers and systems with more accuracy in clinical therapy systems where accurate power deposition into the target tissues may help avoid unwanted results of ultrasound therapy procedures.

SUMMARY

Embodiments hereof are directed to systems and methods for providing an image-guided thermal therapy system including an ultrasonic array of transducers operating in a frequency range and power suited for the therapy at hand. In some respects, the present disclosure overcomes the uncertainty and variability associated with physical, design, engineering, and physiological parameters in ultrasound thermal therapy treatments and systems.

One or more aspects of the present disclosure provide a system with a computer controlled or microprocessor controlled RF driving unit that electrically drives piezo electric ultrasound transducer elements in an ultrasound therapy system.

Aspects of the present disclosure are directed to a system for thermal therapy of diseased tissue operating through the application of a plurality of ultrasonic elements in an array, an apparatus for driving and controlling said plurality of ultrasonic elements, the apparatus comprising a computer-based host unit that determines a desired set of driving characteristics with which to drive said plurality of ultrasonic elements; a microprocessor-based controller that receives an output from said host and provides at least signals representing a frequency characteristic and an amplitude characteristic; a frequency control circuit receiving said frequency characteristic signal; an amplitude control circuit receiving said amplitude characteristic signal; a radio frequency (RF) amplifier receiving an output from at least one of said frequency and said amplitude control circuits, and acting on said output from said at least one of said frequency and said amplitude control circuits, to provide an amplified output signal having both frequency and amplitude characteristics corresponding to said frequency characteristic and said amplitude characteristic; a coupling circuit that receives said amplified output signal and couples the same to a corresponding plurality of said ultrasonic elements in said array; said coupling circuit further providing at least one forward output signal to a first RF detector circuit and at least one reverse output signal to a second RF detector circuit; and a converter that receives an output of said at least first and second RF detector circuits and provides a corresponding converted output to said microprocessor-based controller.

Yet other embodiments are directed to method for ultrasound thermal therapy in a patient, comprising determining a desired therapeutic result of said therapy; inserting a thermal therapy apparatus into an orifice in said patient; positioning said thermal therapy apparatus in said patient so that an ultrasonic array of transducer elements is substantially located within a volume of diseased tissue of said patient; determining a driving frequency and amplitude or power level with which to drive each of the transducer elements of said array; sensing a forward driving signal delivered to each of said elements of said array; sensing a reverse signal from each of said elements of said array; providing said forward and said reverse signals as inputs to a microprocessor; and generating in said microprocessor output signals to control at least a frequency with which to drive said elements of said array.

Other aspects coordinate the driving of the ultrasound apparatus to achieve the desired thermal therapy through accurate and controlled frequency, waveform, and/or amplitudes of the driving signals.

Proper feedback and real-time monitoring may be used in conjunction with the driving and control of the therapy apparatus.

BRIEF DESCRIPTION OF THE DRAWINGS

For a fuller understanding of the nature and advantages of the present invention, reference is be made to the following detailed description of preferred embodiments and in connection with the accompanying drawings, in which:

FIG. 4 illustrates an exemplary sequence for a method used in ultrasound thermal therapy.

DETAILED DESCRIPTION

As discussed above, better understanding of the electrical response of ultrasound transducers in therapeutic systems is useful for improving the effectiveness of such systems and delivering safe efficient treatment to patients.

In some aspects, the present system and method tune an ultrasound thermal therapy apparatus during operation so that the elements of an array of ultrasound sources in the thermal therapy apparatus are optimally or usefully driven with respect to the electrical, acoustic, and mechanical conditions in which they are operating. These conditions may change during the course of a treatment and the present system can adapt to these changes automatically.

By way of an example, the temperature of the patient's tissue being treated and which surrounds an ultrasound applicator (e.g., in the prostate) rises as a result of delivery of ultrasound energy to the patient. The temperature rise causes changes in the acoustic characteristics of the tissue and of the components of the therapy applicator apparatus. The sound speed and acoustic impedance and/or electrical impedances involved can vary as the treatment progresses. Since the transducers are usually relatively thin chips of crystal material sandwiched between an external surface and an internal surface, the thickness of the transducers may change with changing temperature. If not accounted for, this change could de-tune the system because the change in thickness may change the resonance frequency of a transducer. Therefore, a single pre-determined driving frequency and amplitude may not always be optimum for the condition of a given transducer element in an array of such elements. Rather, slight changes in the driving signals can be accomplished to keep the transducers each tuned to a most efficient driving set of parameters so as to best deliver ultrasound energy to the patient in a safe, controllable, predictable, and power efficient way.

In some aspects, the forward electrical power and signal provided to each transducer element in an array is sensed. And in addition, a backward or reverse electrical signal from each transducer is also sensed. These signals can inform a microprocessor whether the ultrasound elements are properly or optimally driven, and if not, can effect changes to the driving frequency and/or power for the respective elements of the array to enhance the efficiency and effectiveness of the driving signals to the elements of the array.

Figure 1:
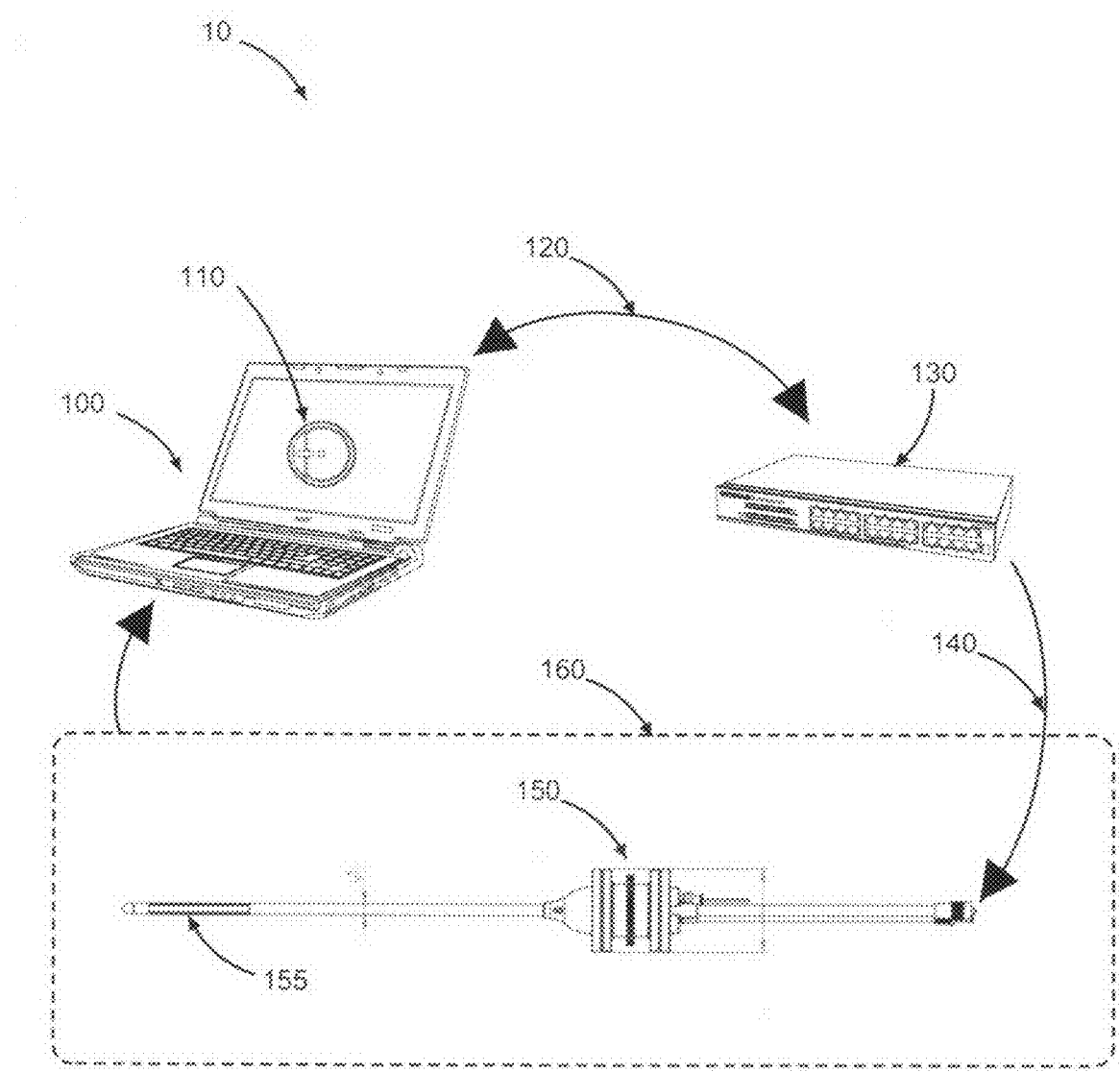
FIG. 1 illustrates an exemplary system for providing image-guided ultrasound therapy to a patient.

FIG. 1 illustrates an exemplary system 10 for providing image-guided ultrasound therapy to a patient. The simplified illustration shows a master computer 100, such as a portable PC, workstation, or other processing device having a processor, memory, and coupled to some input/output apparatus. Master computer 100 may include a display and may support a user interface 110 to facilitate control of and observation of the thermal therapy treatment process.

Master computer 100 is adapted for coupling to other systems and components through a computer interface connector 120. Connection 120 carries data and information to and from master computer 100 and may comprise standard or special-purpose electrical wiring connection cables, such as serial connection cables or the like. Also, connection 120 may be achieved wirelessly as known to those skilled in the art of wireless communication, and may further be achieved by way of multiple connections, over a network, or by another suitable method.

In some embodiments, master computer 100 is coupled through connection 120 to a power control unit 130. Power control unit 130 may be implemented as a stand-alone hardware apparatus but may be implemented as a part of master computer 100, e.g., by being built onto a special card in a computer or server system that accommodates such hardware components.

Power control unit 130 may specifically include at least a processor adapted for processing machine or program instructions, which may be provided to the processor from another component of system 10 and may be stored on a memory device in power control unit 130. Circuitry including analog and/or digital circuitry may be operated within power control unit 130 so as to determine an output power to one or more ultrasound therapy transducer elements in an ultrasound therapy apparatus 150.

In some embodiments, power control unit 130 may deliver controlled electrical driving signals to a plurality of ultrasound transducer elements (e.g., PZT array elements) in ultrasound therapy apparatus 150. The driving signals may be controlled to deliver a programmed amount of power to each element or to groups of elements of therapy apparatus 150. The driving signals may also be controlled so as to provide a determined driving voltage, current, amplitude, waveform, or frequency to said ultrasonic transducers of therapy apparatus 150. Such electrical driving signals are carried from power control unit 130 to the ultrasound therapy apparatus 150 over suitable wires, cables, or buses 140. Appropriate plug interfaces or connectors may be included so as to mate the various ends of the connectors or buses to and from their associated components.

In operation, ultrasound therapy apparatus 150 includes a portion 155 that is inserted into a portion of a patient's body to deliver a suitable dose of ultrasound energy to tissue in a diseased region of the patient's body.

The patient and the ultrasound therapy apparatus 150 are generally disposed in an imaging volume 160 such as a magnetic resonance imaging (MRI) apparatus, which can provide real-time images of the relevant parts of the patient, e.g., the treatment volume to master computer 100 or display and user interface 110. In some embodiments, real-time monitoring of the thermal therapy is performed so that a clinical operator can monitor the progress of the therapy within the treatment volume or diseased tissue. Manual or automated changes can be made to the power signals from power control unit 130 based on input from the results and progress of the treatment.

The feedback and coupling of the treatment system components to the control components in system 10 can be used to ensure that an optimum radio frequency (RF) power signal is provided to each element of an ultrasound array 155 used in treatment of diseased tissues. Some examples include treatment of prostate cancer tumors in male patients using MRI guided ultrasound therapy applications.

RF power control unit 130 may include separate circuit cards having individual processors, amplifiers, filters and other components to achieve the desired driving power output to the elements of ultrasound array 155 of ultrasound treatment apparatus 150. Alternatively, a single processor may be employed to control the behavior of the various power channels to each array element.

Figure 2:
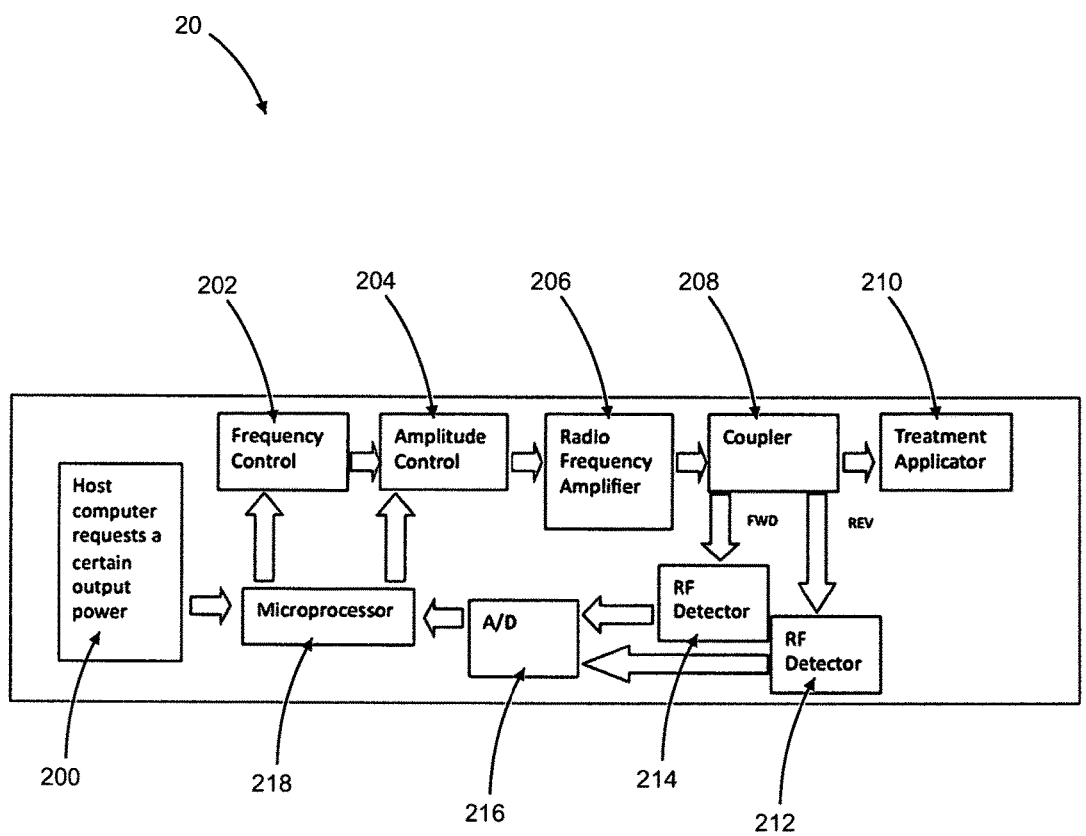
FIG. 2 illustrates an exemplary block diagram of a RF controller apparatus for controlling power to an ultrasound therapy apparatus.

FIG. 2 illustrates an exemplary block diagram 20 showing the workings of a system for controlling the RF driving power to elements of an ultrasound treatment apparatus. At 200, a host computer, which may be similar to master computer 100 of FIG. 1, requests a certain output power. The requested output power may be an output power required by an entire treatment apparatus, a single transducer element, or a group of elements. The power needed to accomplish an effective and safe ultrasound therapy treatment may involve the determination of actual power to be emitted from the array or elements of the array.

The host computer delivers the instruction or request for a certain driving power signal to microprocessor 218, which may be implemented in an integrated circuit (IC) within a RF power control unit, an application-specific IC (ASIC), or similar circuit that operates upon instructions, optionally from a group of instructions stored in some digital memory device in or coupled to microprocessor 218.

Microprocessor 218 provides an input signal to frequency control 202 and amplitude control 204 units. In some embodiments, the amplitude control unit 204 receives the microprocessor 218 output signal as well as an output signal from the frequency control unit 202.

According to one or more embodiments, amplitude control unit 204 provides an output to a radio frequency (RF) amplifier 206. A radio frequency (RF) amplifier 206 amplifies the amplitude of the driving signal to a level that is useful for driving the physical transducer elements of the ultrasound therapy system.

A coupler 208 is provided to couple the output driving signals from the RF amplifier 206 to the treatment applicator 210 (or ultrasound array thereof). The forward and reverse powers from coupler 208 are provided to RF detectors 214 and 212 respectively, indicative of the actual power available from treatment applicator elements 210.

The RF detectors 212 and 214 provide an output to analog-to-digital (A/D) converter 216, which in turn informs microprocessor 218 of the forward and reverse output conditions at coupler 208. Accordingly, the power provided to treatment applicator 210 can be optimized and tuned to the precise levels needed to achieve a safe and effective and reproducible ultrasound thermal therapy procedure. While MRI-based thermometry of a patient (e.g. of his prostate during treatment) may require a relatively long time (many seconds, several seconds), the present concepts allow rapid control of the power and frequency characteristics of said apparatus in the context of thermal therapy to the prostate.

In some embodiments, microprocessor 218 may be in communication with host computer 200 to allow a more precise treatment routine in real-time, and/or to permit logging and recording of the specific electrical and physical conditions prevailing during the ultrasound therapy procedure.

In one or more embodiments, microprocessor 218 is programmed with the expected output power to the ultrasound treatment applicator. The power control unit is designed to output the expected power using the frequency control 202 and the amplitude control 204 blocks using the feedback from the RF detectors 212 and 214. Some embodiments provide the microprocessor 218 with an algorithm that takes the existing output power, the expected output power and the RF detector values for the forward and reverse readings and outputs the appropriate amplitude using a proportional control loop with delay. The algorithm may be implemented through a combination of hardware and software (instructions executed by the hardware).

A control loop using a proportional integral derivative (PID) controller may be employed for the present purpose in some embodiments. To reduce the noise inherent in these readings, the averaging of all inputs, or a select plurality of inputs, may be done with a circular buffer of individual readings. In some embodiments, the only aspect of the amplifier that is tightly calibrated are the RF detectors, but this is not required in all embodiments.

Figure 3:
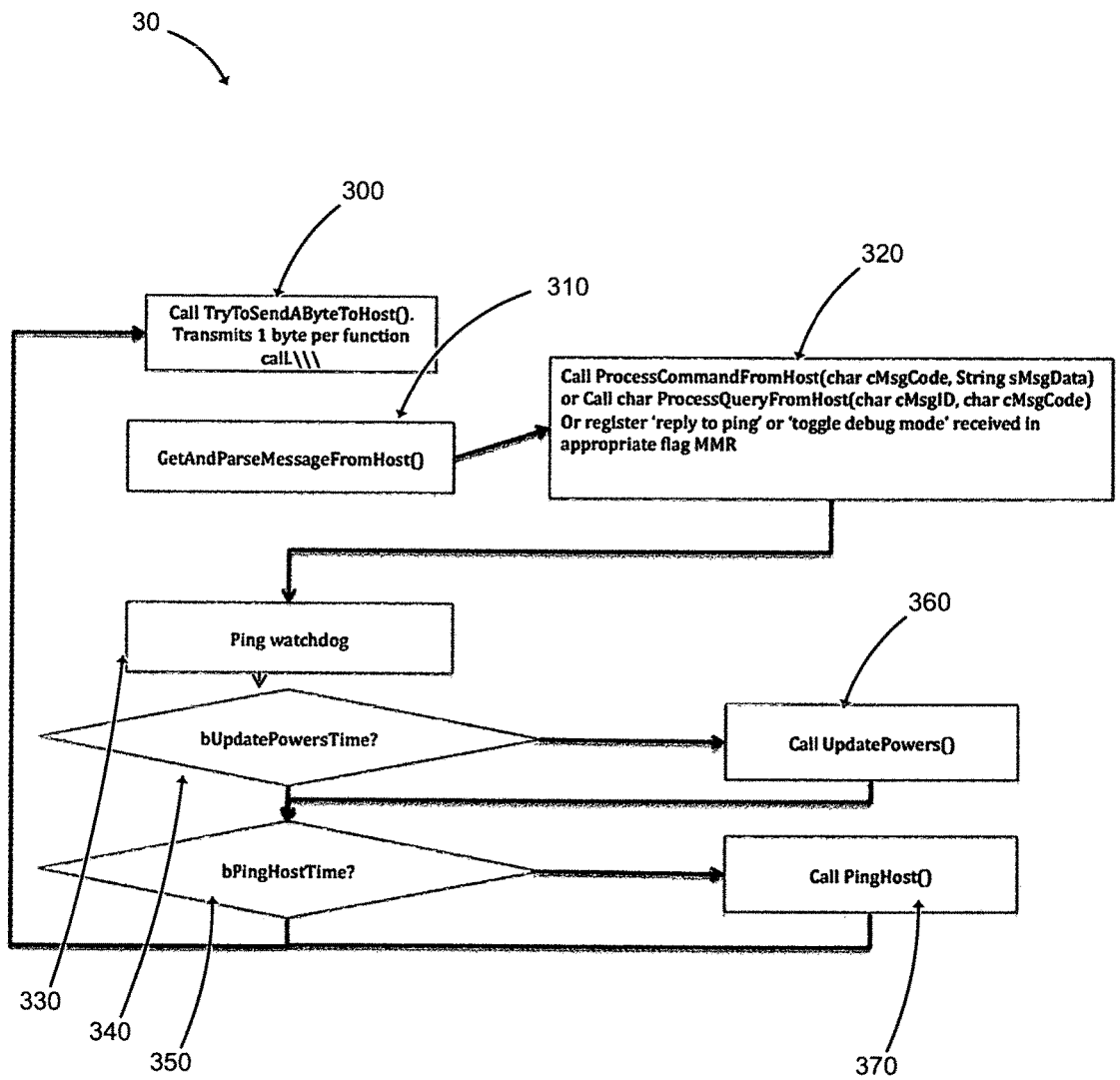
FIG. 3 illustrates an exemplary logic flow diagram in an image-guided ultrasound therapy system.

FIG. 3 illustrates an exemplary logic flow diagram 30 used in determining and controlling the driving power signals to drive the ultrasound therapy apparatus of a therapy system in a selected embodiment.

The illustrated flow diagram is merely exemplary in that many other steps may be performed in addition to those shown. Also, other steps may be substituted for the shown steps, and the ordering of the steps may be accomplished in any way necessary to achieve a given outcome in certain situations. Nonetheless, messages, data and signals are passed between modules of the process so as to maintain proper operation of a RF power control system. The blocks 300-370 perform various exemplary tasks such as setting power parameters, passing information to control and monitor, pinging to confirm proper operation, and so on.

FIG. 4 illustrates an exemplary sequence for a method 40 used in ultrasound thermal therapy consistent with the above discussion. In some illustrative situations a therapy system comprises about 12 channels corresponding to about 12 ultrasonic transducer elements that can be individually driven by the present RF driving power controller. The net power is computed using the forward and reverse signals of the above apparatus. The actual power to the system can be increased or decreased incrementally as necessary to within some set tolerance for example.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An apparatus for driving and controlling a plurality of ultrasonic elements in an array in a system for thermal therapy of diseased tissue operating through the application of the plurality of ultrasonic elements in the array, the apparatus comprising:
   a computer-based host unit that determines a desired set of driving characteristics with which to drive said plurality of ultrasonic elements;
   a microprocessor-based controller that receives an output from said host and provides at least signals representing a frequency characteristic and an amplitude characteristic;
   a frequency control circuit in electrical communication with said controller, said frequency control circuit configured to receive said frequency characteristic signal from said controller and to provide a first output signal;
   an amplitude control circuit in electrical communication with said controller, said amplitude control circuit configured to receive said amplitude characteristic signal from said controller and to provide a second output signal;
   a radio frequency (RF) amplifier in electrical communication with said frequency and said amplitude control circuits, said RF amplifier configured to act on said first output signal and said second output signal and to provide an amplified output signal having both frequency and amplitude characteristics corresponding to said frequency characteristic and said amplitude characteristic;

a coupling circuit in electrical communication with said RF amplifier and said plurality of ultrasonic elements, said coupling circuit configured to receive said amplified output signal and to couple the same to a corresponding plurality of said ultrasonic elements in said array;

a first RF detector circuit in electrical communication with said coupling circuit, said first RF detector circuit configured to sense a forward RF power delivered to each of said ultrasonic elements;

a second RF detector circuit in electrical communication with said coupling circuit, said second RF detector circuit configured to sense a reverse RF power from each of said ultrasonic elements; and an analog-to-digital converter that receives outputs of said first and second RF detector circuits and provides a corresponding converted output to said microprocessor-based controller, said converted output corresponding to said forward RF power and said reverse RF power sensed by said first and second RF detector circuits;

wherein the microprocessor-based controller tunes at least one of said frequency characteristic and said amplitude characteristic according to said forward RF power and said reverse RF power.

2. The apparatus of claim 1, said frequency control circuit further providing an output to said amplitude control circuit.

3. The apparatus of claim 1, said converted output comprising a digital output suitable for use by said microprocessor-based controller.

4. The apparatus of claim 1 said microprocessor-based controller comprising a proportional integral derivative controller.

5. The apparatus of claim 1 said microprocessor-based controller comprising an application-specific integrated circuit.

6. A method for ultrasound thermal therapy in a patient, comprising:

determining a desired therapeutic result of said therapy;

inserting a thermal therapy apparatus into an orifice in said patient;

positioning said thermal therapy apparatus in said patient so that an ultrasonic array of transducer elements is at least partially located within a volume of diseased tissue of said patient;

in a computer-based host unit, determining a driving frequency and amplitude or power level with which to drive each of the transducer elements of said array to achieve said desired therapeutic result;

providing host output signals from said host unit to a microprocessor-based controller, said host output signals representing said driving frequency and said amplitude or said power level;

in a frequency control circuit, receiving said host output signal representing said driving frequency, said frequency control circuit further providing a first output signal;

in an amplitude control circuit, receiving said host output signal representing said amplitude or said power level, said amplitude control circuit further providing a second output signal;

providing said first output signal and said second output signal to a radio frequency (RF) amplifier in electrical communication with said frequency control circuit and said amplitude control circuit, said RF amplifier acting on said first output signal and said second output signal to provide an amplified output signal having both frequency and amplitude characteristics corresponding to said frequency characteristic and said amplitude characteristic;

providing said amplified output signal to a corresponding plurality of said ultrasonic elements in said array;

in a first RF detector circuit, sensing a forward RF power delivered to each of said elements of said array;

in a second RF detector circuit, sensing a reverse RF power from each of said elements of said array;

providing said forward and said reverse RF power as inputs to said controller; and generating in said controller, using said inputs, control output signals to control at least said frequency with which to drive said elements of said array.

7. The method of claim 6, further comprising making temperature measurements in said diseased tissue and adjusting at least said amplitude with which to drive said elements of said array.

8. The method of claim 6 further comprising averaging said forward driving signals.

9. The method of claim 6 further comprising averaging said reverse signals.

10. The method of claim 6 further comprising generating said control output signals based at least in part on an expected output power to said array.

11. The method of claim 6 further comprising generating said control output signals based at least in part on an existing output power of said array.

12. The method of claim 6 further comprising generating said control output signals based at least in part on said forward driving signals and said reverse signals.

13. The method of claim 6 further comprising generating in said microprocessor output signals to control at least said amplitude with which to drive said elements of said array.

14. The method of claim 13 further comprising generating said output signals with a proportional integral derivative controller.

* * * * *